United States Patent
Tenney (10) Patent No.: US 7,357,042 B2
(45) Date of Patent: Apr. 15, 2008

(54) FILTER CONTAMINATION CONTROL DEVICE

(75) Inventor: Douglas A. Tenney, North Reading, MA (US)

(73) Assignee: Cytyc Corporation, Marlborough, MA (US)

( * ) Notice: Subject to any disclaimer, the term of this patent is extended or adjusted under 35 U.S.C. 154(b) by 0 days.

(21) Appl. No.: 11/292,845

(22) Filed: Dec. 1, 2005

(65) Prior Publication Data

US 2007/0125187 A1    Jun. 7, 2007

(51) Int. Cl.
*G01N 1/00* (2006.01)

(52) U.S. Cl. .................................................. 73/863.25

(58) Field of Classification Search ............. 73/864.32, 73/864.23, 864.25, 864.03, 864.73, 864.74, 73/864.72, 863.25; 138/96 R, 109
See application file for complete search history.

(56) References Cited

U.S. PATENT DOCUMENTS

| | | | |
|---|---|---|---|
| 3,343,422 A * | 9/1967 | McSmith ................. | 73/864.03 |
| 3,985,032 A * | 10/1976 | Avakian .................. | 73/863.25 |
| 5,143,627 A | 9/1992 | Lapidus et al. | |
| 5,303,713 A * | 4/1994 | Kurose ....................... | 600/576 |
| 5,364,597 A | 11/1994 | Polk, Jr. et al. | |
| 5,503,802 A | 4/1996 | Polk, Jr. et al. | |
| 5,772,818 A | 6/1998 | Polk, Jr. et al. | |
| 6,318,190 B1 | 11/2001 | Radcliffe et al. | |
| 6,572,824 B1 | 6/2003 | Ostgaard et al. | |
| 6,589,484 B2 * | 7/2003 | Buehler ...................... | 422/100 |
| 6,820,507 B2 * | 11/2004 | Seatter .................... | 73/863.81 |

FOREIGN PATENT DOCUMENTS

WO    2005108952 A1    11/2005

OTHER PUBLICATIONS

PCT International Search Report for PCT/US 2006/061007, Applicant Cytyo Corporation, forms PCT/ISA 210 and 220, mailed Oct. 15, 2007, (6 pages).
PCT Written Opinion for PCT/US 2006/061007, Applicant Cytyc Corporation, forms PCT/ISA/237, mailed Oct. 15, 2007. (5 pages).

* cited by examiner

*Primary Examiner*—Robert Raevis
(74) *Attorney, Agent, or Firm*—Vista IP Law Group LLP

(57) ABSTRACT

A biological specimen filter, for use in a biological specimen collection and transfer system having a vacuum source, comprises a tubular body having an exterior surface, an interior chamber, a first end configured to couple to the vacuum source, and a second end having an opening in communication with the chamber, and a fluid trap extending around at least a portion of a circumference of the exterior surface of the tubular body and sized and shaped to catch fluid flowing along the exterior surface as the tubular body is inverted from a first position, in which the opening is submerged in a fluid source, to a second position, in which the opening is removed from the fluid source.

12 Claims, 12 Drawing Sheets

FILTER CONTAMINATION CONTROL DEVICE

FIELD OF INVENTION

The present inventions generally relate to devices for collecting and transferring microscopic particles to prepare biological specimens, and more particularly, to devices for controlling contamination associated with such devices.

DESCRIPTION OF RELATED ART

Many medical diagnostic tests, such as pap smears, require a physician to collect cells by brushing and/or scraping a skin or mucous membrane in a target area with an instrument. The collected cells are typically smeared ("fixed") onto a slide, and stained to facilitate examination under a microscope by a cytotechnologist and/or pathologist. For example, a pathologist may employ a polychrome technique, characterized by staining the nuclear part of the cells, to determine the presence of dysplasia or neoplasia. The pathologist may also apply a counter-stain for viewing the cytoplasm of the cells. Because the sample may contain debris, blood, mucus and other obscuring artifacts, the test may be difficult to evaluate, and may not provide an accurate diagnostic assessment of the collected sample.

Cytology based on the collection of the exfoliated cells into a liquid preservative offers many advantages over the traditional method of smearing the cells directly onto the slide. A slide can be prepared from the cell suspension using a filter transfer technique, as disclosed in U.S. Pat. Nos. 6,572,824, 6,318,190, 5,772,818, 5,364,597 and 5,143,627, which are expressly incorporated herein by reference.

Filter transfer methods generally start with a collection of cells suspended in a liquid in a container. These cells may be collected and dispersed into a liquid preservative or they may naturally exist in a collected biological liquid. Dispersion in liquid preservatives containing methanol, such as PreservCyt™ solution, breaks up mucus and lyses red blood cells and inflammatory cells, without affecting the cells of interest. A filter cartridge with a fixed diameter aperture covered by a membrane is submerged into the liquid in the container. Subsequently, the liquid is drawn across the membrane and into the filter cartridge to concentrate and collect the cells on the membrane. Debris, such as lysed blood cells and dispersed mucus, which flow through the pores of the membrane, are not collected on the membrane and are greatly reduced in the collected specimen by the combined methods of dispersion and filtering.

The cells collected on the membrane are transferred onto a slide for further processing, such as visual examination. To facilitate this transfer of collected cells from membrane to slide, an arm repositions the membrane of the filter cartridge close to a slide. The arm removes the filter cartridge from the liquid filled container, and moves and rotates it. When the filter cartridge is removed from the liquid, some of the liquid clings to the outside of the filter cartridge. When the filter cartridge is moved and rotated, this liquid may drip and contaminate the arm, which is non-disposable.

Contamination has at least two consequences. First, some biological samples are very inconvenient if not impossible, to re-harvest. While it is highly inconvenient for a patient to repeat a pap smear, it is may not be possible to repeat a biopsy on a mole that has been removed to test for malignancy. Second, for those situations where a second sample collection is not a viable option, chain of custody issues can have serious repercussions. Such chain of custody issues can call into doubt entire batches of test results and, in the worst cases, all results from a clinical lab.

In order to minimize contamination by liquid clinging to the outside of the filter cartridge, some filter transfer devices include an absorbent pad attached to the arm in order to catch any dripping liquid. Such pads can consist of a porous polyethylene treated with a surfactant to improve absorbency. For cell based studies, such pads have been proven to be effective for preventing contamination. For DNA based studies, concerns have been raised about the efficacy of using such pads to prevent contamination.

Alternatively, in semi-automatic filter transfer devices, the interface with the filter cartridge can be repeatedly removed and cleaned. However, this alternative is difficult to implement in a fully automatic device and it is labor intensive. Further, repeated cleaning reduces the life expectancy of the rubber o-rings sealing the interface.

SUMMARY OF THE INVENTION

In some embodiments, a biological specimen filter, for use in a biological specimen collection and transfer system having a vacuum source, comprises a tubular body having an exterior surface, an interior chamber, a first end configured to couple to the vacuum source, and a second end having an opening in communication with the chamber, and a fluid trap extending around at least a portion of a circumference of the exterior surface of the tubular body and sized and shaped to catch fluid flowing along the exterior surface as the tubular body is inverted from a first position, in which the opening is submerged in a fluid source, to a second position, in which the opening is removed from the fluid source.

The fluid trap is disposed proximate the first end of the tubular body and comprises an absorbent ring. The fluid trap also comprises a channel, with either a u-shaped or v-shaped cross-section, in which the absorbent ring is disposed. The fluid trap may comprise a flange attached to the exterior surface of the tubular body or it may be integrally formed from the tubular body.

In some embodiments, a biological specimen collection and transfer system, comprises a biological specimen slide processor, including a grasper configured to submerge an open end of a specimen filter into a fluid source, withdraw the open end of the specimen filter from of the fluid source, and invert the specimen filter, and a fluid trap extending around at least a portion of a circumference of the exterior surface of the tubular body and sized and shaped to catch fluid flowing along the exterior surface as the tubular body is inverted by the grasper.

In some embodiments, a biological specimen filter device for use in a biological specimen collection and transfer system, the system including a vacuum source, the specimen filter comprises a tubular body having an exterior surface, an interior chamber, a first end configured to couple to the vacuum source, and a second end having an opening in communication with the chamber, and an absorbent member disposed around at least a portion of a circumference of the exterior surface of the tubular body and sized and shaped to catch fluid flowing along the exterior surface as the tubular body is inverted from a first position, in which the opening is submerged in a fluid source, to a second position, in which the opening is removed from the fluid source.

BRIEF DESCRIPTION OF THE DRAWINGS

In order to better understand and appreciate the invention, reference should be made to the drawings and accompany detailed description, which illustrate and describe exemplary embodiments thereof. For ease in illustration and understanding, similar elements in the different illustrated embodiments are referred to by common reference numerals. In particular.

DETAILED DESCRIPTION OF THE ILLUSTRATED EMBODIMENTS

In the following description of the illustrated embodiments, it will be understood by those skilled in the art that the drawings and specific components thereof are not necessarily to scale, and that various structural changes may be made without departing from the scope or nature of the various embodiments.

Figure 1:
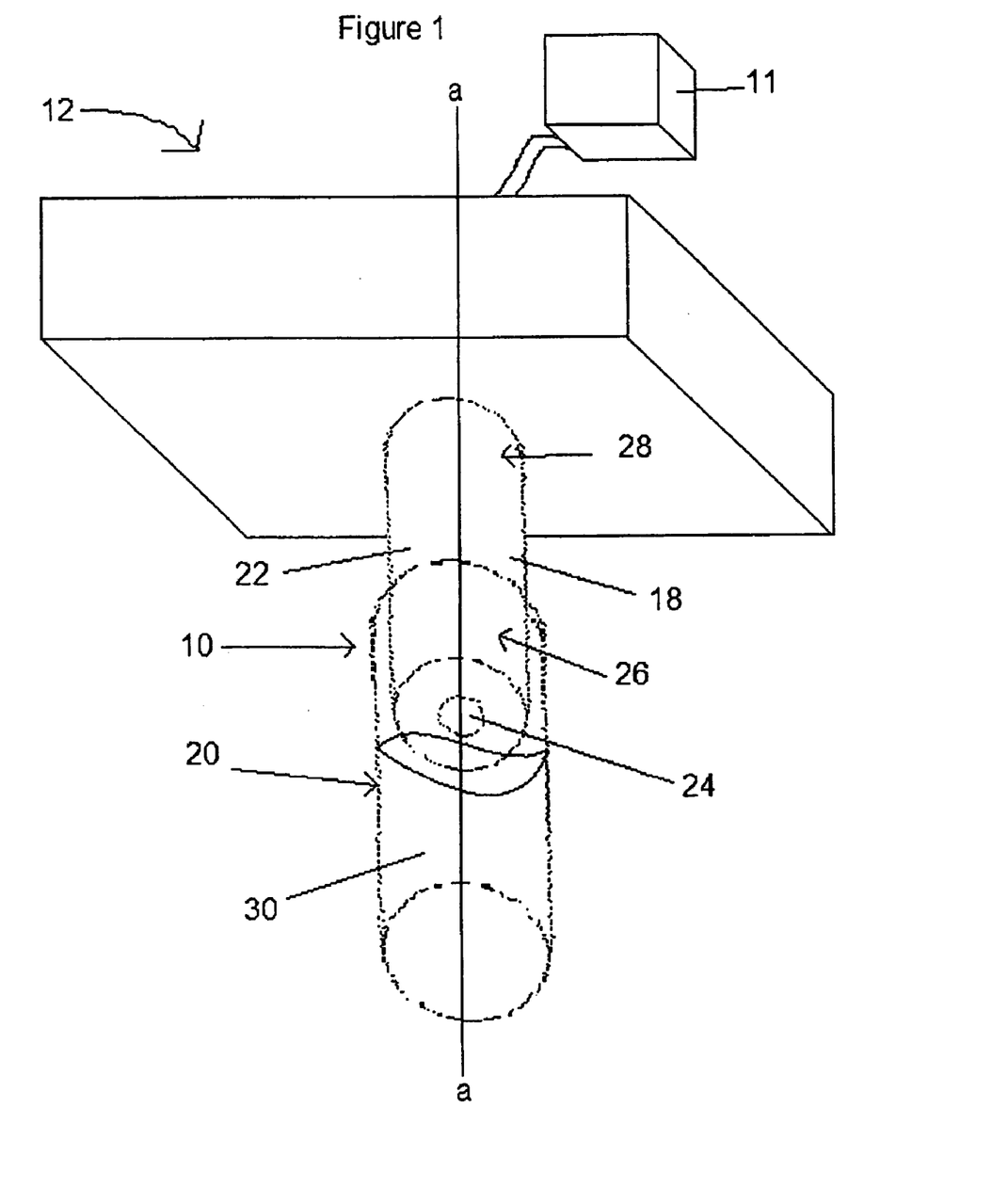
FIG. 1 is a perspective view of an exemplary filter/container interface of a biological specimen collection and transfer system, in which the filter is positioned to collect a biological specimen.
Figure 2:
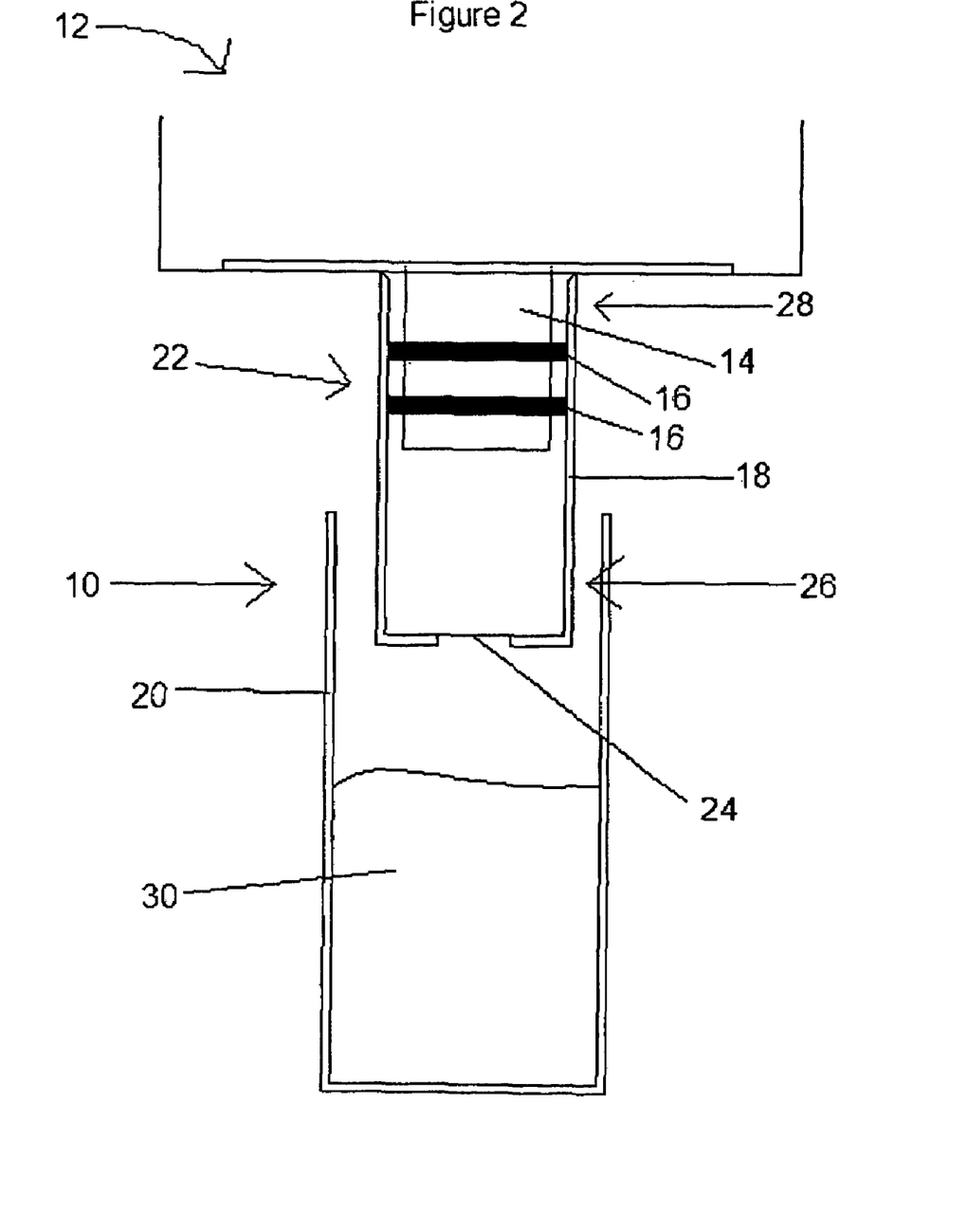
FIG. 2 is a cross sectional view of the filter/container interface of FIG. 1 through line a-a.

Referring to FIGS. 1 and 2, a filter/container interface 10 of a biological specimen collection and transfer system 12 is shown. In this embodiment, the filter/container interface 10 includes a stem 14, air tight seals 16, a filter cartridge 18, and a sample container 20. The stem 14 is connected, with the air tight seals 16, to the filter cartridge 18. The stem 14, in turn, is connected to a vacuum source 11.

The filter cartridge 18 includes a tubular body 22 with a membrane 24 at a second end 26 and a first end 28 configured to connect to the stem 14. The second end 24 is configured to be submerged into a liquid 30 containing a biological specimen (not shown), such as collected cervical cells. The sample container 20 holds the liquid 30.

The membrane 24 takes the form of a porous polycarbonate membrane treated with a wetting agent, as commercially available from manufacturers to be hydrophilic. The membrane 24 is on the order of seven microns thick, and is available commercially from Poretics Corporation, Livermore, Calif. 94550, and from Nuclepore Corporation, Pleasanton, Calif. 94566. The tubular body 22 is molded as a single piece, from polystyrene resin marketed by the Dow Chemical Company under the designation Styron 685D. Consequently, there are no seams between these parts that may leak under pressure during use of the filter device. Alternatively, however, the tubular body 22 may be initially formed as separate pieces and then bonded together.

Figure 3:
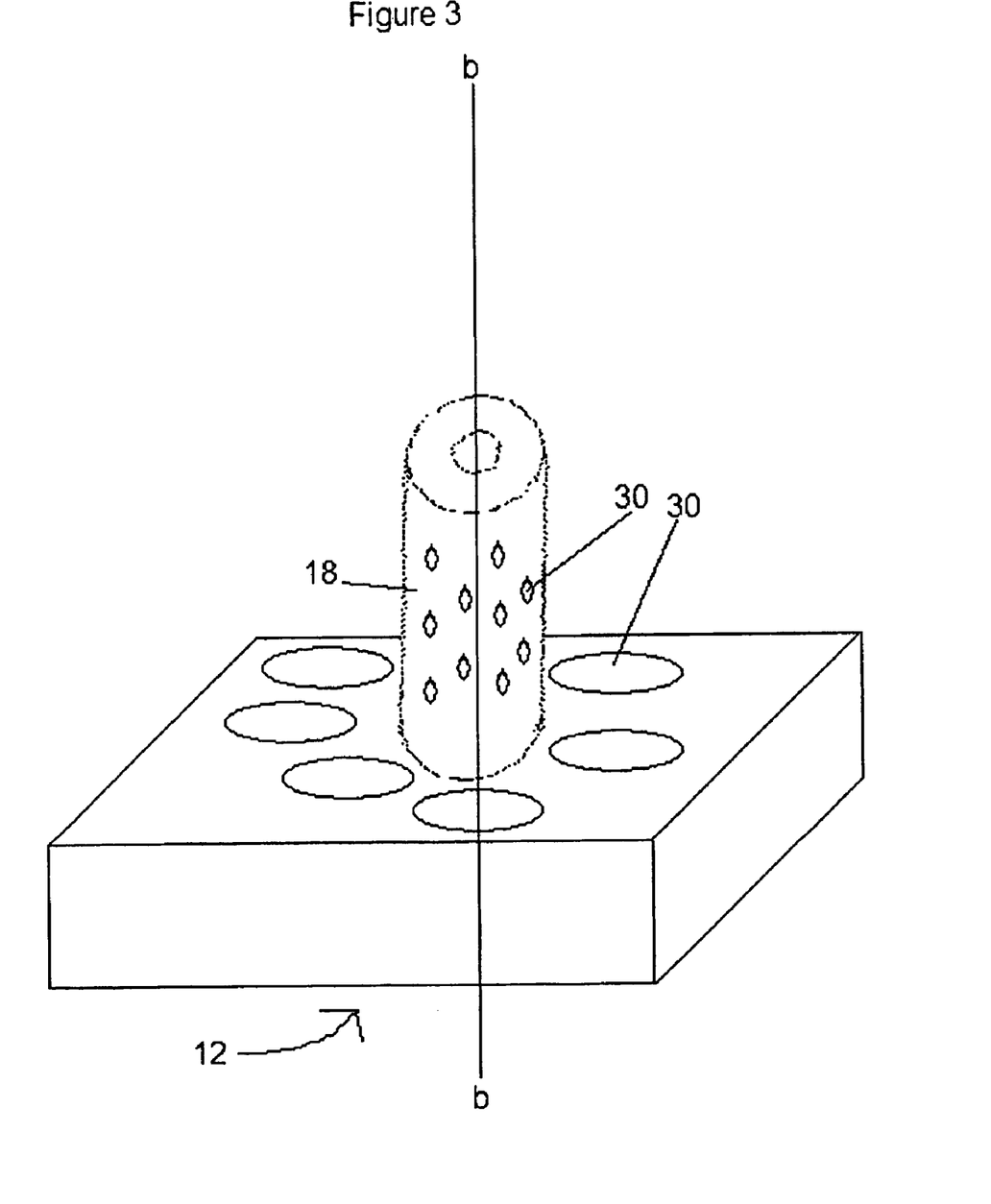
FIG. 3 is a perspective view of an exemplary filter/stem interface of a biological specimen collection and transfer system, in which the filter is positioned to transfer a biological specimen.
Figure 4:
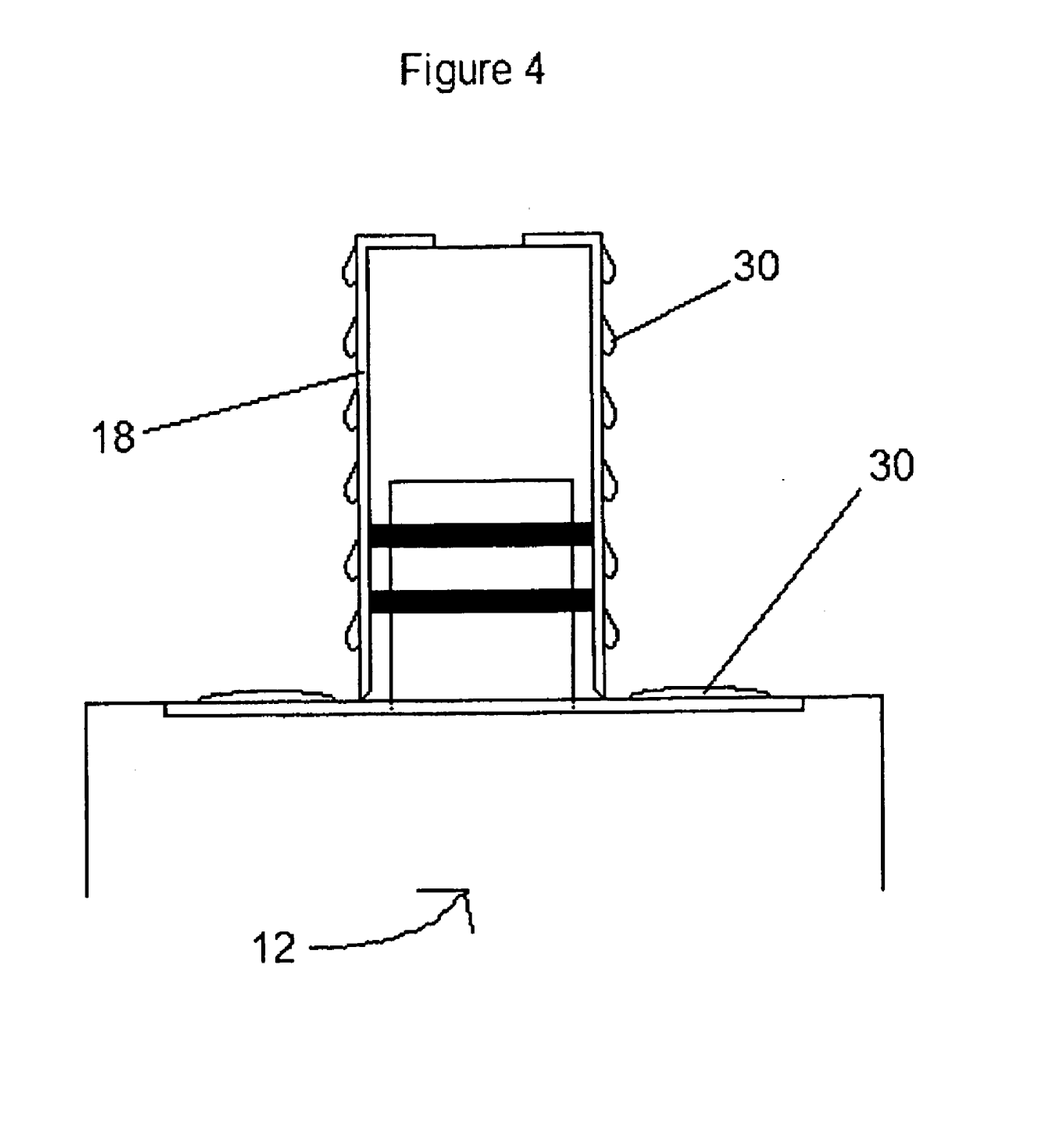
FIG. 4 is a cross sectional view of the filter/stem interface of FIG. 3 through line b-b.

During collection of the biological specimen, the second end 26 of the tubular body 22 is first submerged into the liquid 30 in the sample container 20 then withdrawn out the liquid 30. To prepare to transfer the biological specimen, the filter cartridge 18 is inverted, as shown in FIGS. 3 and 4. Some of the liquid 30 clings to the outside of the filter cartridge 18 and drips onto the collection and transfer system 12. It can be appreciated that this liquid 30 can contaminate the collection and transfer system 12 and other filter cartridges 18 and sample containers 20 that may be used with the collection and transfer system 12.

Figure 5:
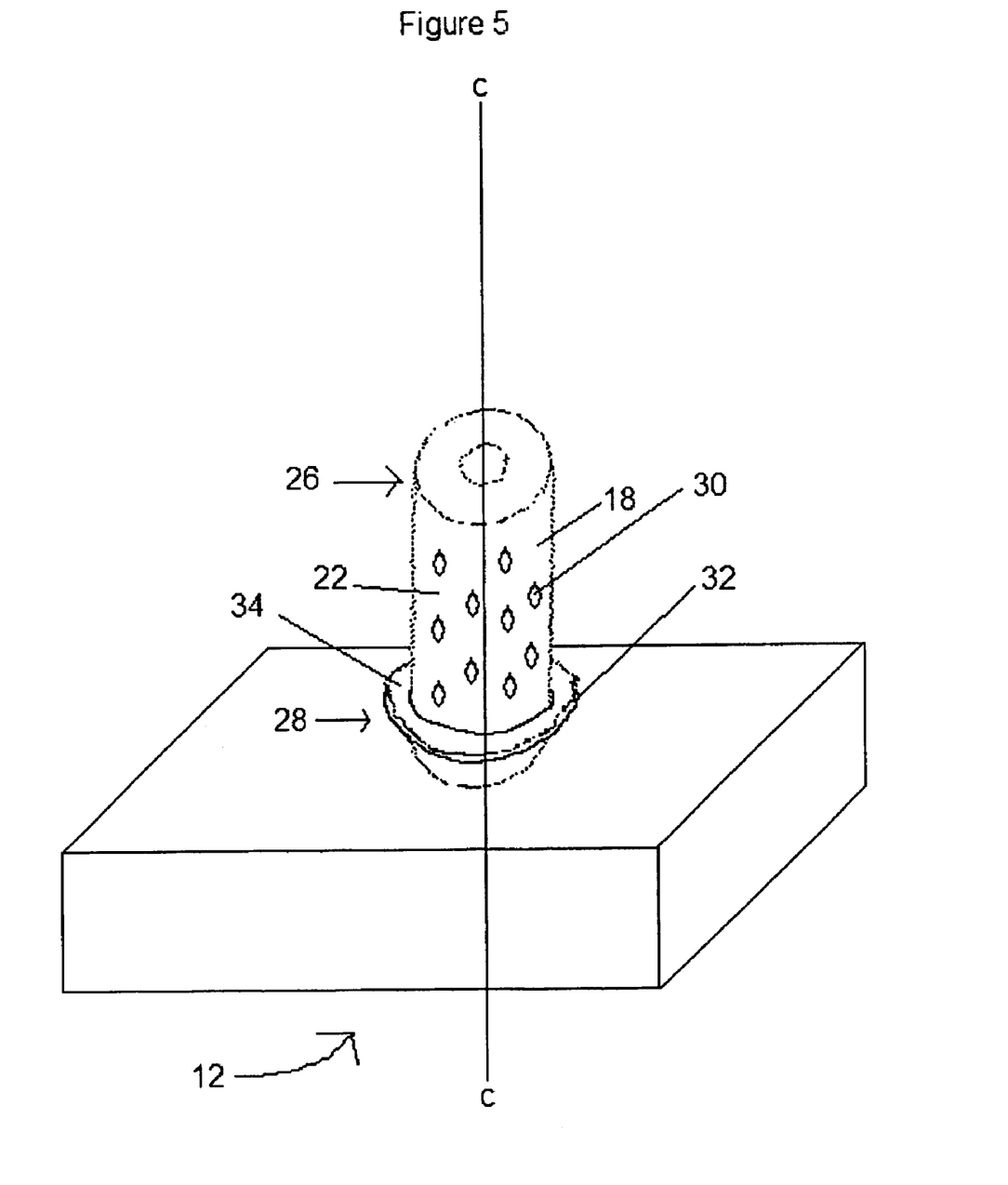
FIG. 5 is a perspective view of an exemplary filter/stem interface of a biological specimen collection and transfer system, in which the filter is positioned to transfer a biological specimen.
Figure 6:
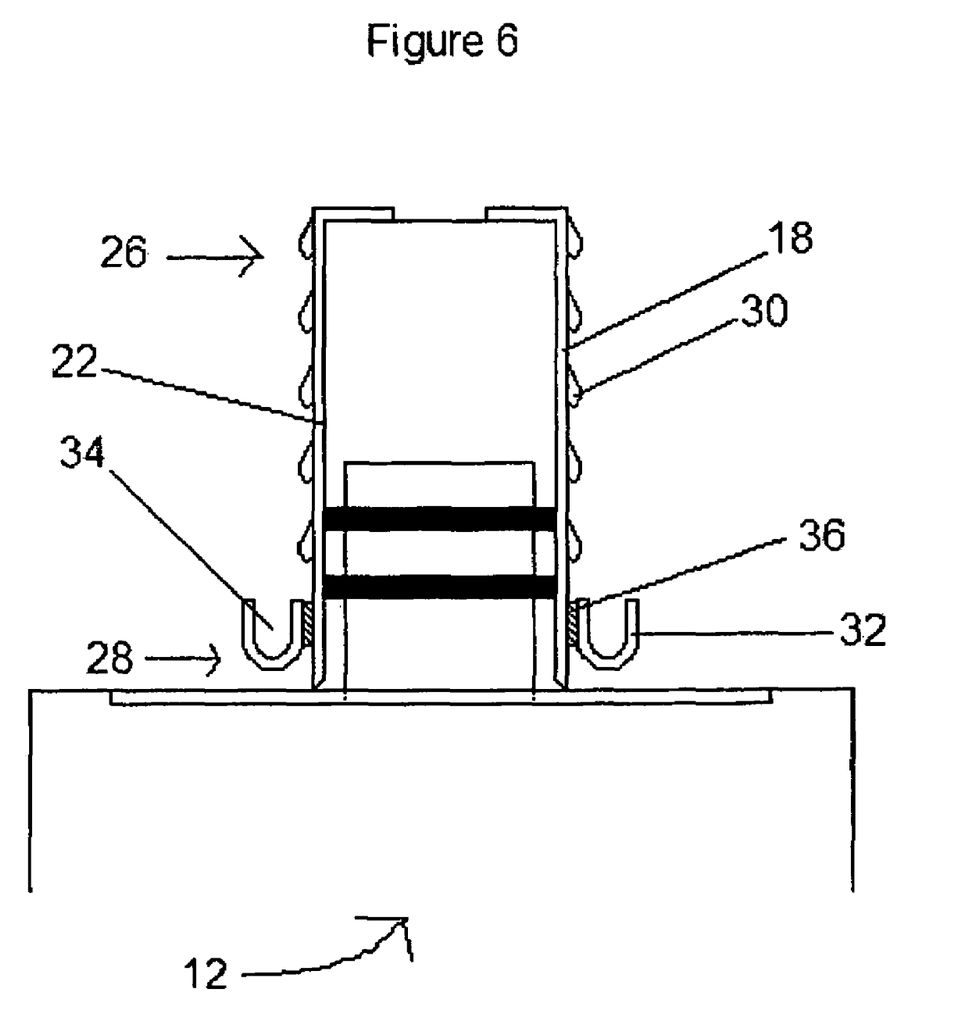
FIG. 6 is a cross sectional view of the filter/stem interface of FIG. 5 through line c-c.

Referring to FIGS. 5 and 6, a filter cartridge 18 is shown with a fluid trap 32 disposed at the first end 28 of the tubular body 22. In this embodiment, the fluid trap 32 is u-shaped, forming an annular cavity 34. Alternatively, the fluid trap 32 can be v-shaped. The fluid trap is bonded to the first end 28 of the tubular body 22 with the cavity 34 open to the second end 26.

The fluid trap 32 is bonded to the tubular body 22 with a bonding chemical 36. Suitable chemicals 36 for bonding include adhesives and solvents that can partially melt the fluid trap 32 and the tubular body 22.

Alternatively, the fluid trap 32 can also be heat bonded or ultrasonically bonded to the tubular body. In heat bonding, the fluid trap 32 is heat welded to the tubular body 22 by a heated ram. A suitable ultrasonic bonding process is available from Polyfiltronics, Inc. of Rockland, Mass. 02370.

When the filter cartridge 18 is removed from the liquid 30 and inverted, as described above, the liquid 30 drips from second end 26 toward the first end 28 and the collection and transfer system 12. The cavity 34 of the unshaped fluid trap 32 catches the dripping liquid 30, minimizing contamination of the collection and transfer system 12. The filter cartridge 18 is disposable and the potentially contaminating liquid 30 is removed when the filter cartridge 18 is ejected.

Figure 7:
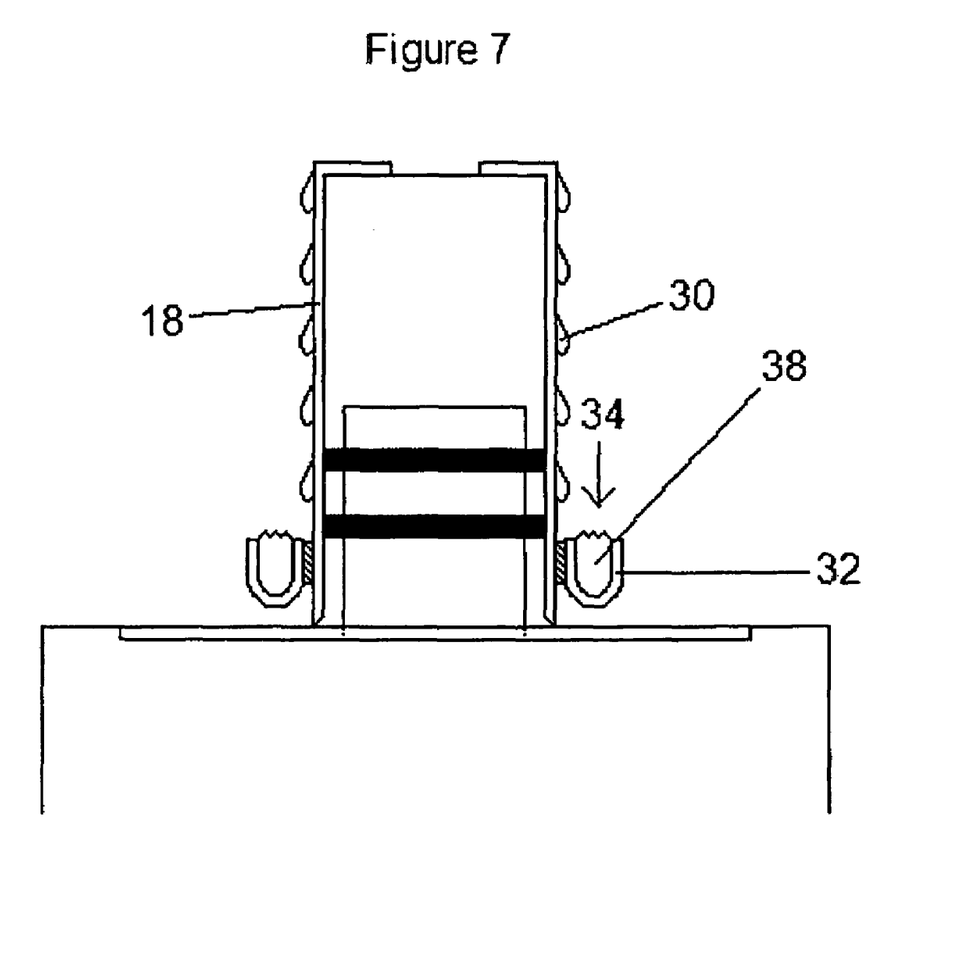
FIG. 7 is a cross sectional view of the filter/stem interface of FIG. 5 through line c-c, in which an absorbent ring is disposed in the u-shaped fluid trap.

In FIG. 7, the filter cartridge 18 has an absorbent annular ring 38 disposed inside of the cavity 34 in the fluid trap 32. The ring 38 is made of porous polyethylene treated with a surfactant to increase absorption. The ring 38 holds the liquid 30 in place to further minimize spillage and contamination.

Figure 8:
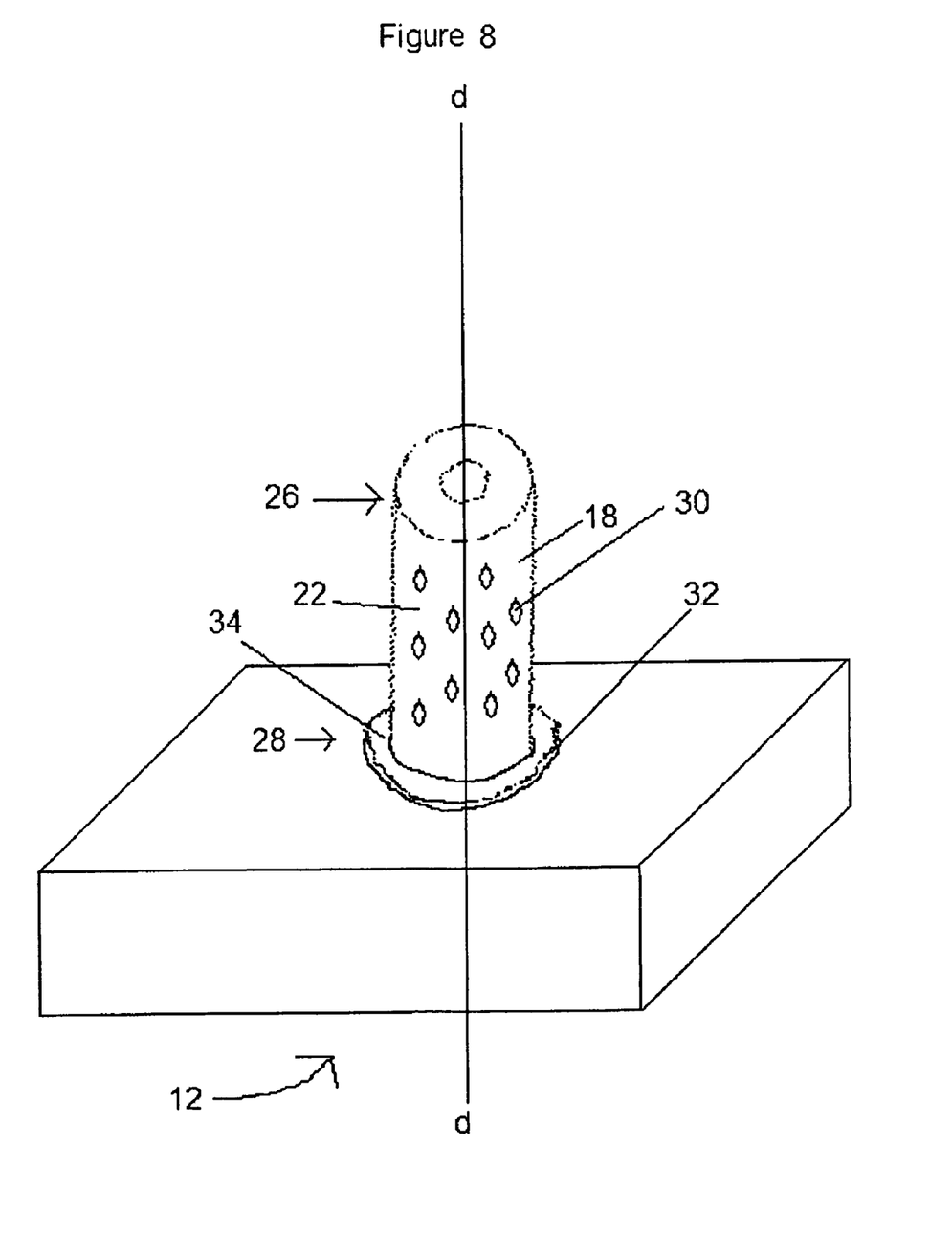
FIG. 8 is a perspective view of an exemplary filter/stem interface of a biological specimen collection and transfer system, in which the filter is positioned to transfer a biological specimen.
Figure 9:
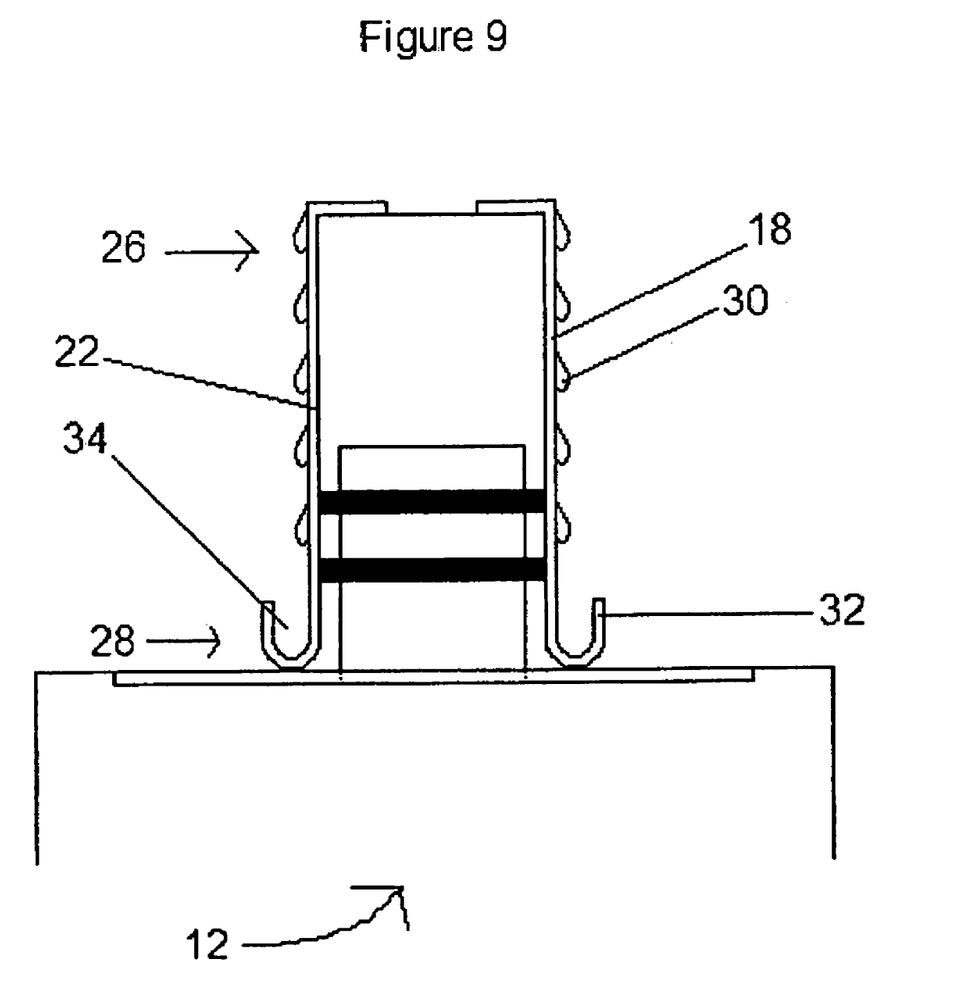
FIG. 9 is a cross sectional view of the filter/stem interface of FIG. 8 through line d-d.
Figure 10:
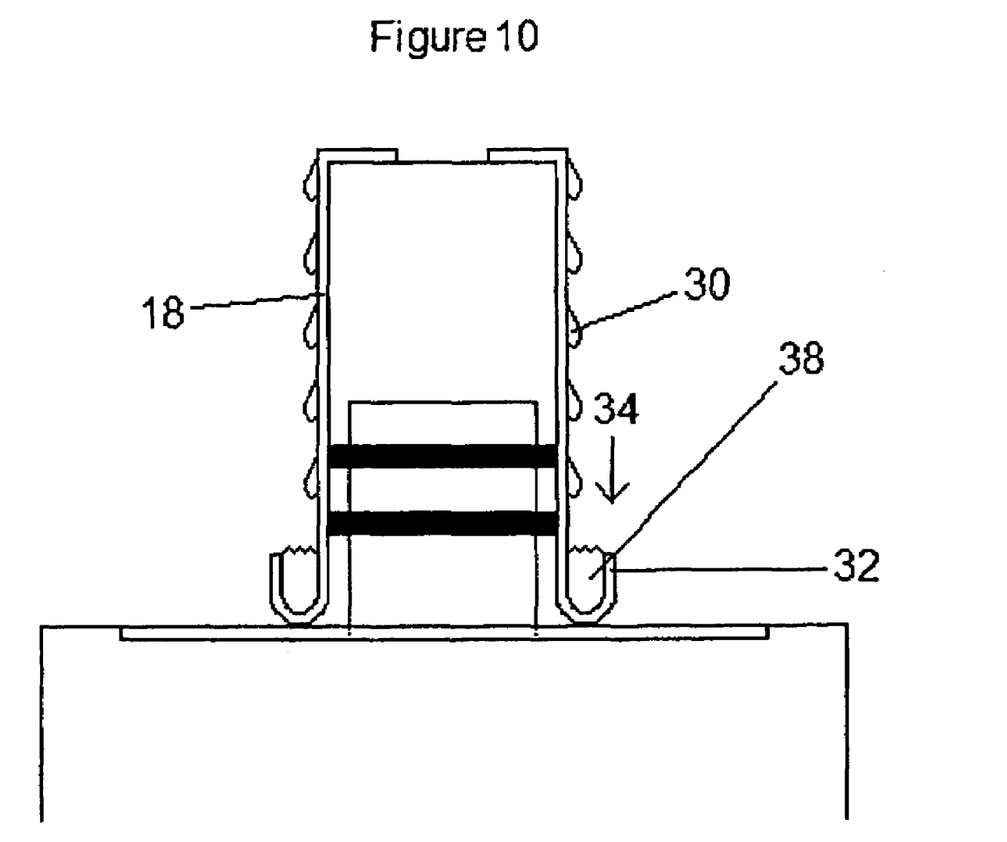
FIG. 10 is a cross sectional view of the filter/stem interface of FIG. 8 through line d-d, in which an absorbent ring is disposed in the u-shaped fluid trap.

Instead of bonding the fluid trap 32 to the tubular body 22, the fluid trap 32 can be formed as part of the tubular body 22, as shown in FIGS. 8, 9 and 10. While these figures show a fluid trap 32 formed into the extreme first end 28 of the tubular body 22, the fluid trap 32 can be alternatively formed anywhere in the first end 28 of the tubular body. Other than being formed as part of the tubular body 22, the fluid trap 32 functions as described above to minimize contamination of the collection and transfer system 12.

Figure 11:
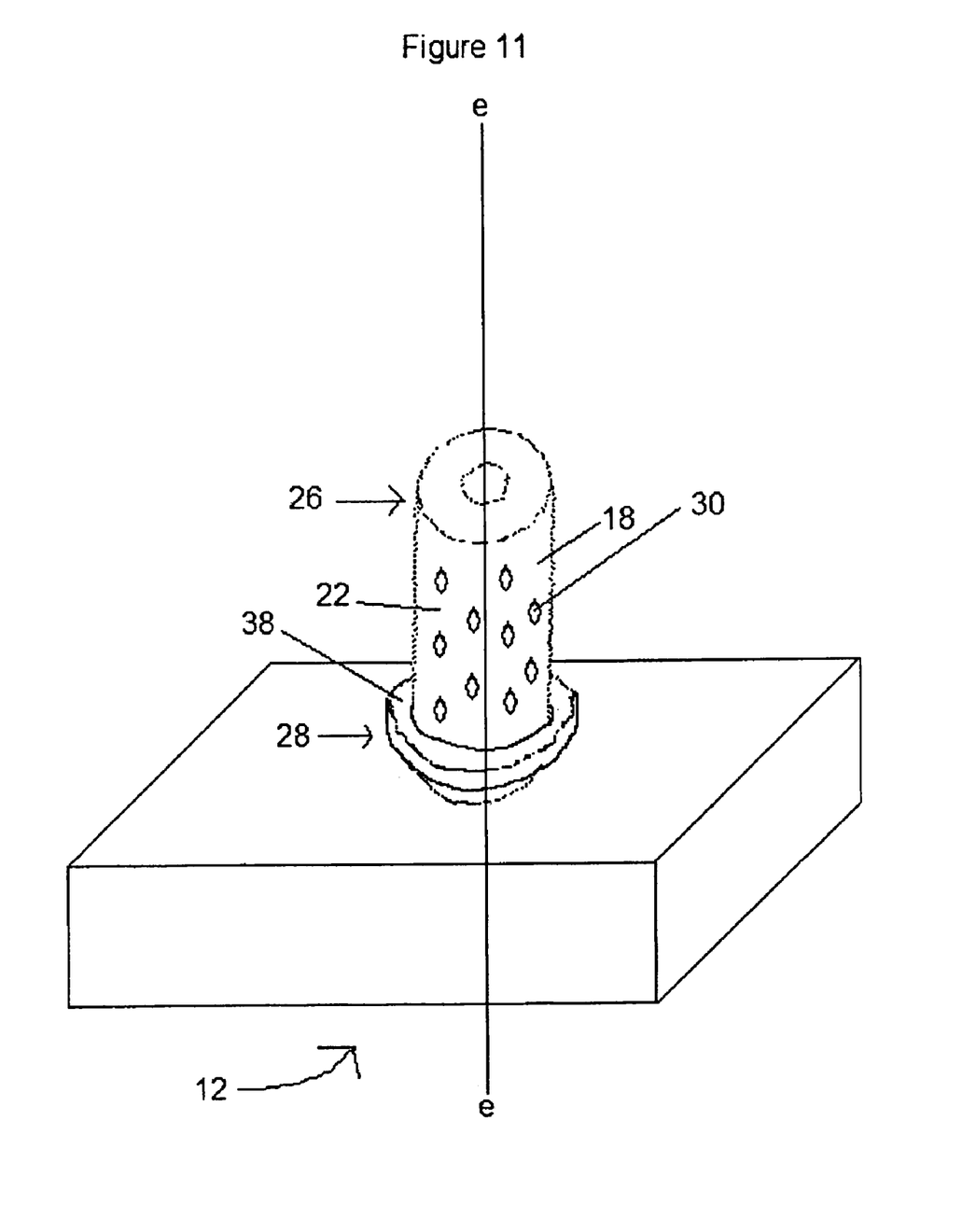
FIG. 11 is a perspective view of an exemplary filter/stem interface of a biological specimen collection and transfer system, in which the filter is positioned to transfer a biological specimen.
Figure 12:
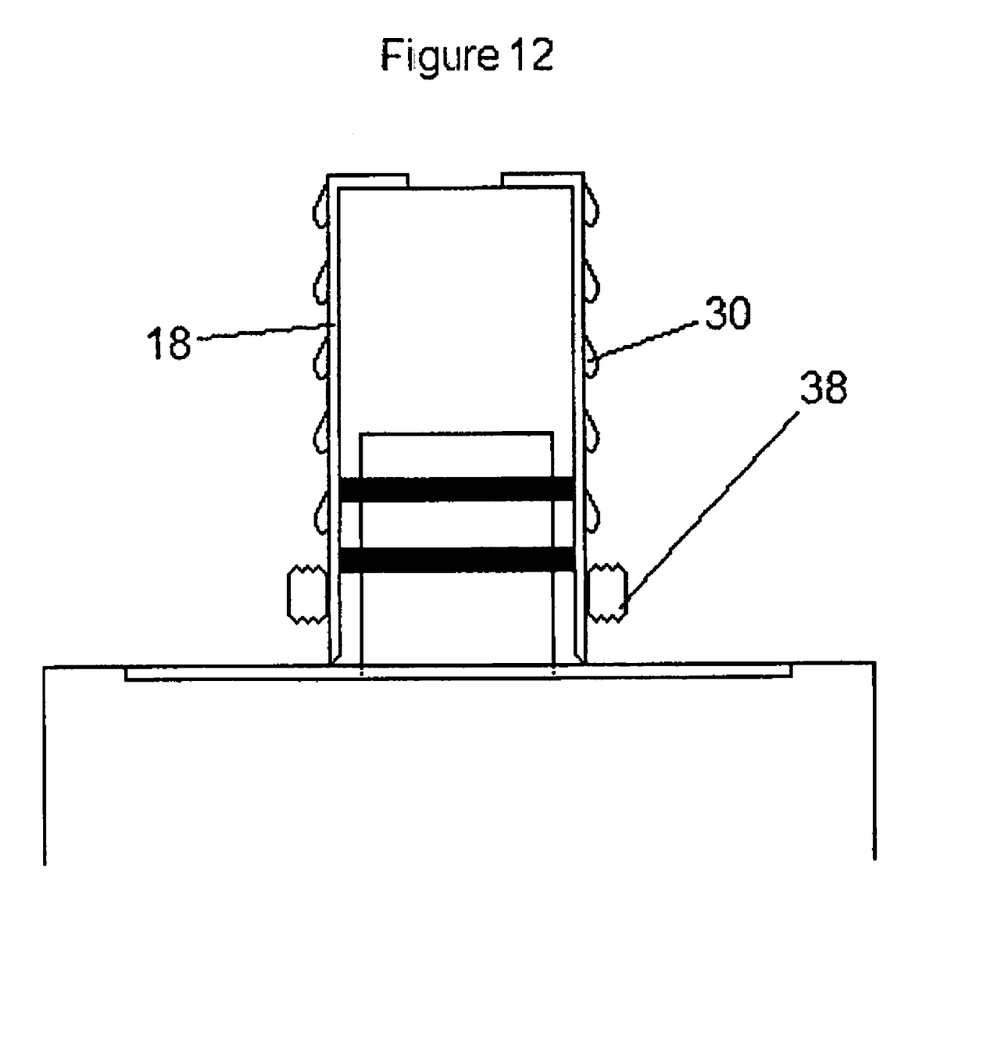
FIG. 12 is a cross sectional view of the filter/stem interface of FIG. 11 through line e-e, in which an absorbent ring is disposed around the filter cartridge.

In FIGS. 11 and 12, the absorbent annular ring 38 is disposed around the filter cartridge 18. The ring 38 is stretchable and it is slightly smaller than the circumference of the filter cartridge 18. Consequently, when the ring 38 is stretched around the filter cartridge 18, as shown in FIG. 11, the ring 38 exerts an inwardly directed radial force that holds the ring 38 onto the filter cartridge 18.

Although various embodiments of the invention have been shown and described herein, it should be understood that the above description and figures are for purposes of illustration only, and are not intended to be limiting of the invention, which is defined only by the appended claims and their equivalents.

What is claimed is:

1. A biological specimen filter for use in a biological specimen collection and transfer system, the system including a vacuum source, the specimen filter comprising:
   a tubular body having an exterior surface, an interior chamber, a first end configured to couple to the vacuum source, and a second end having an opening in communication with the chamber;
   a membrane positioned within the tubular body and extending across the opening of the tubular body at the second end, the membrane having a porosity to allow fluid to be drawn across the membrane and into the tubular body to collect cells on the membrane; and
   a fluid trap bonded to the tubular body and extending around at least a portion of a circumference of the exterior surface of the tubular body and sized and shaped to catch fluid flowing along the exterior surface as the tubular body is inverted from a first position, in which the opening is submerged in a fluid source, to a second position, in which the opening is removed from the fluid source.

2. The biological specimen filter device of claim 1, wherein the fluid trap is disposed proximate the first end of the tubular body.

3. The biological specimen filter device of claim 1, the fluid trap comprising a channel.

4. The biological specimen filter device of claim 3, wherein the channel has a u-shaped cross-section.

5. The biological specimen filter device of claim 3, wherein the channel has a v-shaped cross-section.

6. The biological specimen filter device of claim 1, the fluid trap comprising a flange attached to the exterior surface of the tubular body.

7. A biological specimen filter device for use in a biological specimen collection and transfer system, the system including a vacuum source, the specimen filter comprising:
   a tubular body having an exterior surface, an interior chamber, a first end configured to couple to the vacuum source, and a second end having an opening in communication with the chamber;
   a membrane positioned within the tubular body and extending across the opening of the tubular body at the second end, the membrane having a porosity to allow fluid to be drawn across the membrane and into the tubular body to collect cells on the membrane; and
   a fluid trap bonded to the tubular body, an absorbent member being positioned in the fluid trap and being disposed around at least a portion of a circumference of the exterior surface of the tubular body and sized and shaped to catch fluid flowing along the exterior surface as the tubular body is inverted from a first position, in which the opening is submerged in a fluid source, to a second position, in which the opening is removed from the fluid source.

8. The biological specimen filter device of claim 1, wherein a thickness of the membrane is about seven microns.

9. The biological specimen filter device of claim 1, wherein the tubular body has a cylindrical shape, and a diameter of the first end is approximately the same as a diameter of the second end.

10. The biological specimen filter device of claim 1, wherein the fluid trap is chemically bonded to the exterior surface of the tubular body.

11. The biological specimen filter device of claim 1, wherein the fluid trap is ultrasonically bonded to the exterior surface of the tubular body.

12. The biological specimen filter device of claim 1, wherein the fluid trap is heat bonded to the exterior surface of the tubular body.

* * * * *